(12) United States Patent
Murthy et al.

(10) Patent No.: US 8,309,077 B2
(45) Date of Patent: Nov. 13, 2012

(54) STABILIZED BACTERIOPHAGE FORMULATIONS

(75) Inventors: Kishore Murthy, Ottawa (CA); Rainer Engelhardt, Ottawa (CA)

(73) Assignee: CHR. Hansen A/S, Horsholm (DK)

( * ) Notice: Subject to any disclaimer, the term of this patent is extended or adjusted under 35 U.S.C. 154(b) by 0 days.

(21) Appl. No.: 11/666,709

(22) PCT Filed: Nov. 2, 2005

(86) PCT No.: PCT/CA2005/001678
§ 371 (c)(1), (2), (4) Date: Oct. 9, 2007

(87) PCT Pub. No.: WO2006/047870
PCT Pub. Date: May 11, 2006

(65) Prior Publication Data
US 2008/0038322 A1 Feb. 14, 2008

Related U.S. Application Data

(60) Provisional application No. 60/624,576, filed on Nov. 2, 2004.

(51) Int. Cl.
*A01N 63/00* (2006.01)
*A61K 39/12* (2006.01)

(52) U.S. Cl. ..................... 424/93.6; 435/5; 435/235.1

(58) Field of Classification Search .................. None
See application file for complete search history.

(56) References Cited

U.S. PATENT DOCUMENTS

| | | | |
|---|---|---|---|
| 5,736,388 A * | 4/1998 | Chada et al. | 435/320.1 |
| 6,187,313 B1 * | 2/2001 | Segelman | 424/764 |
| 6,485,902 B2 | 11/2002 | Waddell et al. | |
| 6,703,040 B2 | 3/2004 | Katsarava et al. | |
| 6,929,798 B2 | 8/2005 | Pillich et al. | |
| 2002/0015720 A1 * | 2/2002 | Katsarava et al. | 424/426 |
| 2003/0027241 A1 | 2/2003 | Sayler et al. | |
| 2003/0109025 A1 | 6/2003 | Durand et al. | |
| 2003/0113293 A1 * | 6/2003 | Bermudes et al. | 424/93.2 |
| 2004/0208854 A1 | 10/2004 | Waddell et al. | |
| 2004/0247569 A1 * | 12/2004 | Morris et al. | 424/93.6 |
| 2008/0318311 A1 | 12/2008 | Murthy et al. | |
| 2009/0130196 A1 | 5/2009 | Murthy et al. | |

FOREIGN PATENT DOCUMENTS

| | | |
|---|---|---|
| EP | 0 403 292 | 12/1990 |
| WO | WO 98/05344 A | 2/1998 |
| WO | WO 01/51066 | 7/2001 |
| WO | WO 03/093462 | 11/2003 |
| WO | WO 2004/045645 | 6/2004 |
| WO | WO 2004/064732 | 8/2004 |

OTHER PUBLICATIONS

Matsuzaki et al., Bacteriophage therapy: a revitalized therapy against bacterial infectious diseases, 2005, Journal of Infectious Chemotherapy, vol. 11, pp. 211-219.*
Cole, Liquid filled and sealed hard gelatin capsules, 2000, Capsugel Product Sheet, Capsugel Library, pp. 1-12.*
Langer, New Methods of Drug Delivery, 1990, Science, vol. 249, No. 4976, pp. 1527-1533.*
Bennett, A. R. et al., "The Use of Bacteriophage-based Systems for the Separation and Concentration of *Salmonella*," Journal of Applied Microbiology, Aug. 1997, vol. 83, No. 2, pp. 259-265, Search Report.
Jepson, C. D. et al., "Bacteriophage Lambda is a Highly Stable DNA Vaccine Delivery Vehicle," Vaccine, 2004, vol. 22, No. 19, pp. 2413-2419, Search Report.
Orlova, Z. N. et al., "The Use of Tablet-Form Polyvalent Bacteriophage with an Acidfast Coating in the Treatment of Children with Dysentery," VOPR OKHR Materin Det. Mar. 1970, vol. 15, No. 3, pp. 25-29, Search Report.
Prouty, C. C., "Storage of the Bacteriophage of the Lactic Acid *Streptococci* in the Desiccated State with Observations on Longevity," Appl Microbiol., 1953, vol. 1, pp. 250-251, Search Report.
Sergienko, F. E., "Dry Bacteriophages, Their Preparation and Use," Microbiology and Epidemiology, Edited by E. B. Babsky et al., Medical Publications, Ltd., London, Nov. 1945, pp. 116-123, Search Report.
Stone, Richard, "Stalin's Forgotten Cure," Science, Oct. 2002, vol. 298, No. 5594, pp. 728-731, Search Report.
Sulakvelidze, Alexander, "Bacteriophage Therapy," Antimicrobial Agents and Chemotherapy, Mar. 2001, vol. 45, No. 3, pp. 649-659, Search Report.
Thiel, Karl, "Old Dogma, New Tricks-21st Century Phage Therapy," Nature Biotechnology, Jan. 2004, vol. 22 No. 1, pp. 31-36, Search Report.
Supplementary European Search Report for European Application No. 05 80 9909.4-2112/1833497; Date of Completion: Aug. 31, 2009.
Office Action dated Apr. 15, 2009 for U.S. Appl. No. 11/666,709, filed Oct. 9, 2007.
Matsuzaki et al., "Bacteriophage therapy: a revitalized therapy against bacterial infectious diseases," 2005, Journal of Infectious Chemotherapy, 11, pp. 211-219.

\* cited by examiner

*Primary Examiner* — Benjamin P Blumel
(74) *Attorney, Agent, or Firm* — Brinks Hofer Gilson & Lione

(57) ABSTRACT

Stabilized bacteriophage compositions, and methods for preparing stabilized bacteriophage compositions are provided. The method for producing an antibacterial composition involves adsorbing an aqueous solution of one or more bacteriophages, or one or more phage components, onto a matrix to produce a composition, and drying the composition to produce the antibacterial composition. An antibacterial composition comprising one or more strain of bacteriophage, or one or more phage component, adsorbed onto a matrix is also provided. The antibacterial composition, or the antibacterial composition embedded in a solid support, may be used within a cream, lotion or gel, be admixed with a pharmaceutical carrier and administered topically, orally, nasally, used as a powdered inhalant, or the antibacterial composition or encapsulated antibacterial composition, may be added to a feed for animal, aquatic or avian uses.

12 Claims, 4 Drawing Sheets

STABILIZED BACTERIOPHAGE
FORMULATIONS

This application is a National Stage application of International Application No. PCT/CA2005/001678, filed Nov. 2, 2005, which claims the benefit of U.S. Provisional Application No. 60/624,576, filed Nov. 2, 2004, the entire contents of which are hereby incorporated herein by reference in their entirety.

The present invention relates to stabilized bacteriophage formulations and their use as delivery systems. More particularly, the present invention pertains to stabilized bacteriophage formulations, methods for preparing stabilized bacteriophage formulations, and uses of stabilized bacteriophage formulations as delivery systems.

BACKGROUND OF THE INVENTION

Bacteriophage therapy has the potential to provide an effective method to specifically control the multiplication of various strains of bacteria. However, to be commercially viable, the bacteriophages themselves must show a certain degree of stability to allow for storage.

Various methods have been used to store phage, including freezing at low temperatures, lyophilising, and storing in liquid medium. All methods have shown varying degrees of success at maintaining a high titer of viable bacteriophages.

Prouty (1953, Appl Microbiol, 1:250-351) reported that dessicated bacteriophage of lactic acid producing *Streptococci* remained viable at 0° C. for 42 months, at 37° C. for 72 months and at 12° C. and 25° C. for at least 78 months. However, there is no mention of the effect of storing desiccated bacteriophage on the titer of the bacteriophage.

Keogh and Pettingill (1966, Appl Microbiol, 14:4421-424) show that bacteriophages for lactic acid producing *Streptococci* in the presence of whey protein are resistant to freezing and cold storage. Phage stored at 4° C. and −18° C. showed little reduction in the bacteriophage titer; freeze-thaw cycles also showed no significant loss of titer. Warren and Hatch (1969, Appl Microbiol, 17:256-261) report a significant decrease in the titer and viability of a bacteriophage suspension stored (without stabilizers) at 4° C., while storage at −20° C. and 20° C. resulted in the greatest survival of phage. They also report that long term storage of bacteriophages at −20° C. tends to result in the formation of clumps.

Jepson and March (2004, Vaccine, 22:2413-2419) disclose that a liquid suspension of bacteriophages (in either SM buffer or a 1/200 dilution of SM buffer in water) was stable for 6 months at 4° C. and −70° C., with the phage remaining unaffected by freeze-thawing. Increased temperature, between 20° C. and 42° C., resulted in a significant loss of titre. Lyophilisation and immediate reconstitution of bacteriophages in the presence or absence of stabilizers resulted in a loss of titre of 80-95%. Of the bacteriophages remaining following lyophilization in the presence of dry skim milk powder, storage at temperatures between 20° C. and 42° C. resulted in a loss of titre similar to that of the liquid suspension. However, lyophilization in the presence of trehalose resulted in an increase in half-life of bacteriophage between 20° C. and 42° C. The effect of pH of the storage medium was also examined. There was no change in bacteriophage titer over a 24 hour period at pH 3-11. However, the titer dropped rapidly when stored for 5 minutes at pH values below 2.4.

Scott et al (WO 03/093462) discloses the stabilization and immobilization of viruses, including bacteriophage, by covalently bonding the virus to a substrate. This process requires chemicals to activate the substrate and coupling agents to aid in formation of covalent bonds between the substrate and the virus. The use of these reagents increases the expense required for immobilization. Furthermore, the virus or bacteriophage are note able to release to the environment due to their covalent attachment to the substrate. Therefore, the immobilized phage may only act in discreet locations.

Freezing or lyophilisation of bacteriophage suspensions, or bacteriophage suspensions optionally containing stabilizers, are inconvenient methods that require specialized equipment and add to the cost of a commercial preparation. While it is desirable to be able to store bacteriophages in a desiccated state, the process of lyophilization results in a significant loss of titre. Furthermore, the covalent attachment of bacteriophages to a substrate does not allow for the release of the bacteriophages from the substrate and limit its usefulness for our applications. Alternative methods for bacteriophage stabilization are required.

SUMMARY OF THE INVENTION

The present invention relates to stabilized bacteriophage formulations and their use as delivery systems. More particularly, the present invention pertains to stabilized bacteriophage formulations, methods for preparing stabilized bacteriophage formulations, and uses of stabilized bacteriophage formulations.

It is an object of the present invention to provide a stabilized bacteriophage formulation showing improved stability.

The present invention provides a method for producing an antibacterial composition comprising, adsorbing an aqueous solution of bacteriophages, or phage components, onto a solid or powdered matrix to produce composition, and drying the composition to produce an antibacterial composition.

The present invention also pertains to the method described above wherein the matrix may be selected from the group consisting of skim milk powder, soya protein powder, whey protein powder, albumin powder, casein, gelatin, single cell proteins, algal protein, plant peptone, trehalose, mannitol, powdered sugar, sugar alcohol, charcoal, latex beads, a water-soluble carbohydrate-based material, talc, chitin, and fish cartilage.

The present invention also provides an antibacterial composition comprising one or more than one strain of bacteriophage, or phage component, adsorbed onto a matrix.

The present invention includes the antibacterial material as defined above, wherein the soluble matrix is selected from the group consisting of skim milk powder, soya protein, albumin powder, single cell proteins, trehalose, mannitol, sugar and sugar alcohol.

The antibacterial compositions of the present invention are easy to prepare and exhibit the property of being stable over various lengths of time at refrigerator and room temperatures, from about −10° C. to about 25° C., or any amount therebetween. Furthermore, bacteriophages, or phage components, may be readily released from the antibacterial compositions of the present invention with little or no loss in titer. The antibacterial compositions of the present invention may be used within lotions, lubricants, gels and creams, toothpaste, be admixed with a pharmaceutically acceptable carrier for oral, nasal, or topical applications for example but not limited to skin, vaginal, ophthalmic, nasal, aural, anal, rectal, and other types of administration, or be used within wound dressings, and exhibit antimicrobial activity.

The present invention provides stabilized phage preparations in a dry form as a delivery system for powder inhalants. The present invention also provides a suitable matrix for preparing phage or phage compositions for encapsulation and delivery to the gut past the stomach acids.

The antibacterial compositions of the present invention may be used for human, veterinary, agricultural or aquacultural purposes. Furthermore, the compositions as described herein may be used for treatment of trees and plants, and environmental applications. The antibacterial composition may be used within a cream, lotion or gel, be admixed with a pharmaceutical carrier and administered topically, orally, nasally, used as a powdered inhalant, or the antibacterial composition may be added to a feed for animal, aquatic or avian uses.

This summary of the invention does not necessarily describe all necessary features of the invention.

BRIEF DESCRIPTION OF THE DRAWINGS

These and other features of the invention will become more apparent from the following description in which reference is made to the appended drawings wherein.

DESCRIPTION OF PREFERRED EMBODIMENT

Figure 1:
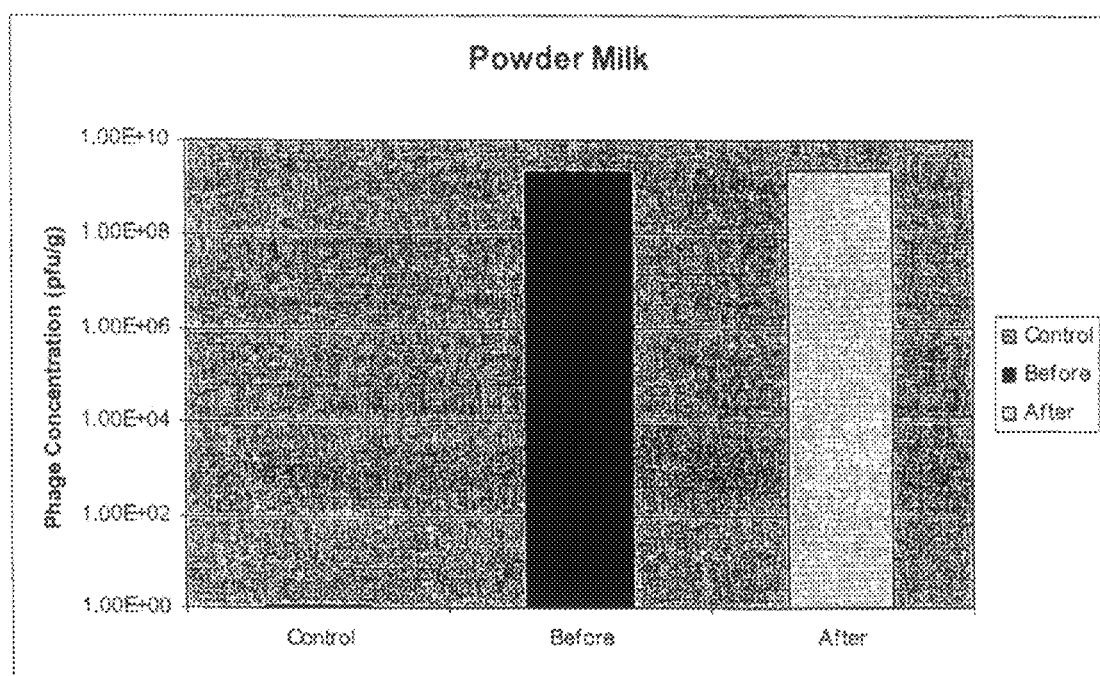
FIG. 1 shows the titer of phage applied to the skim milk powder (Before) and that obtained after immobilization and resuspension (After).
Figure 2:
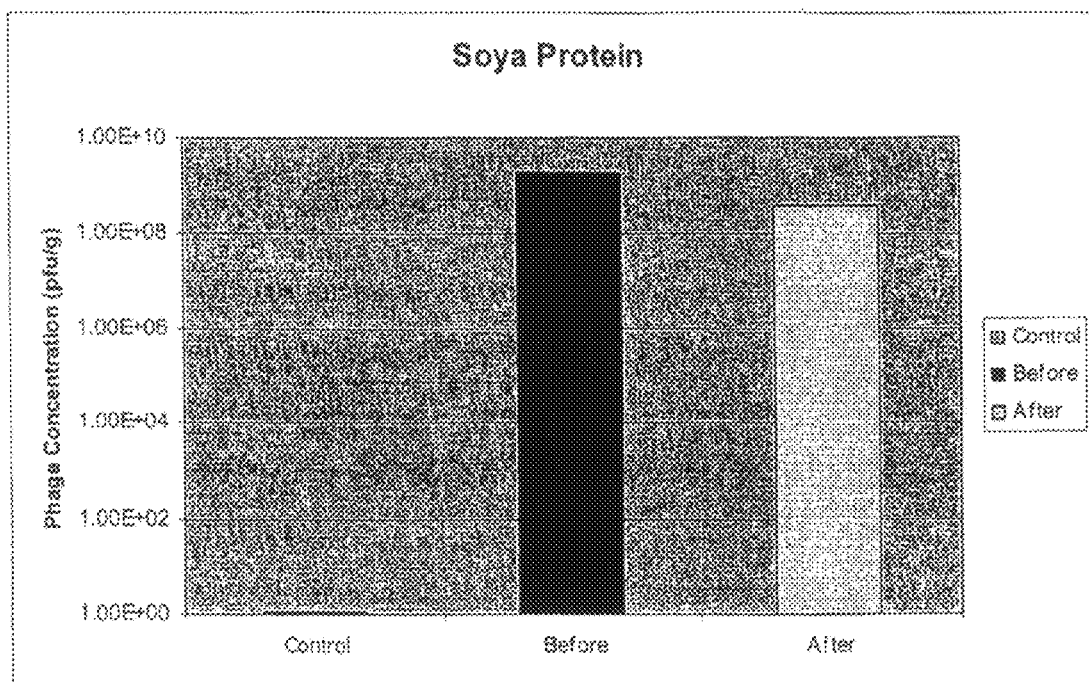
FIG. 2 shows the titer of phage applied to the soya protein powder (Before) and that obtained after immobilization and resuspension (After).

The present invention relates to stabilized bacteriophage formulations. More particularly, the present invention pertains to stabilized bacteriophage formulations, methods for preparing stabilized bacteriophage formulations, and uses of stabilized bacteriophage formulations.

The following description is of a preferred embodiment.

The present invention provides an antibacterial composition comprising one or more than one strain of bacteriophage, one or more than one phage component, or a combination thereof, adsorbed onto a matrix. The present invention also provides a method for producing an antibacterial composition comprising, adsorbing an aqueous solution of bacteriophages, phage component, or a combination thereof, onto a matrix to produce an antibacterial composition, and drying the antibacterial composition. The solution of bacteriophage, phage component, or a combination thereof, may comprise one or more than one strain of bacteriophage, phage component, or a combination thereof that are capable of infecting the same or different bacterial targets. This method is simple to perform, does not require specialized equipment, and bacteriophage, phage components, or a combination thereof, prepared in this manner are stable.

The antibacterial composition may be used in a variety of ways for the control of bacterial growth, and may be used for a variety of applications. For example, which is not to be considered limiting in any manner, the antibacterial compositions may be used for human, veterinary, agricultural and aquacultural applications. Furthermore, the compositions may be used for treatment of trees and plants, and environmental applications. In a further non-limiting example, the antibacterial compositions of the present invention may be used within lotions, lubricants, gels and creams for dermatological or wound applications, applied directly for topical applications, for example but not limited to, applied to skin, vaginal, ophthalmic, nasal, aural, anal, or rectal areas, used within toothpaste or applied onto dental floss for oral hygiene applications. The antibacterial composition may also be applied to a dressing for treating wounds. The antibacterial composition may also be encapsulated and used as a feed additive or as an oral treatment for the control of bacteria within a human, a mammal, or an avian species.

The term "bacteriophage" or "phage" is well known in the art and generally indicates a virus that infects bacteria. Phages are parasites that multiply inside bacterial cells by using some or all of the hosts biosynthetic machinery, and can either be lytic or lysogenic. The bacteriophages used in accordance with the present invention may be any bacteriophage, lytic or lysogenic that is effective against a target pathogen of interest.

By the term "target pathogen" or "target bacteria", it is meant pathogenic bacteria that may cause illness in humans, animals, fish, birds, or plants. The target pathogen may be any type of bacteria, for example but not limited to bacterial species and strains of *Escherichia coli, Streptococci, Humicola, Salmonella, Campylobacter, Listeria, Staphylococcus, Pasteurella, Mycobacterium, Hemophilius, Helicobacter, Mycobacterium, Mycoplasmi, Nesseria, Klebsiella, Enterobacter, Proteus, Bactercides, Pseudomonas, Borrelius, Citrobacter, Propionobacter, Treponema, Chlamydia, Trichomonas, Gonorrhea, Clostridium, Shigella, Enterococcus, Leptospirex, Bacillii* including *Bacillus anthracis* and other bacteria pathogenic to humans, animals, fish, birds, or plants.

By the term "animal" or "animals", it is meant any animal that may be affected by, or carry, a pathogen. For example, but without wishing to be limiting in any manner, animals may include human, poultry, such as chicken or turkey, etc; swine; livestock, which term includes all hoofed animals such a horses, cattle, goats, and sheep, etc; and household pets such as cats and dogs.

Phage specific for one or more than one target pathogen may be isolated using standard techniques in the art for example as taught in Maniatis et al (1982, Molecular cloning: a laboratory manual, Cold Spring Harbor Laboratory, Cold Spring Harbor, N.Y.; which is incorporated herein by reference). If desired, a cocktail of different bacteriophages may be used to target one or more than one pathogen as described herein.

The term "phage component" or "phage components" refers to any phage component including but not limited to the tail, or a phage protein or other molecular assemblage that is effective in killing, reducing growth, or reproduction of a target bacteria, or a plurality of target bacteria.

If desired, a cocktail of bacteriophages, phage components, or both, may be used against a single bacterial target, or multiple bacterial targets. The target bacteria may be any type of bacteria, for example but not limited to the bacterial species and strains of *Escherichia coli, Streptococci, Humicola, Salmonella, Campylobacter, Listeria, Lawsonia, Staphylococcus, Pasteurella, Mycobacterium, Hemophilius, Helicobacter, Mycoplasmi, Nesseria, Klebsiella, Enterobacter, Proteus, Bactercides, Pseudomonas, Borrelius, Citrobacter, Propionobacter, Treponema, Chlamydia, Trichomonas, Gonorrhea, Clostridium, Shigella, Enterococcus, Leptospirex, Bacillii* including *Bacillus anthracis* and other bacteria pathogenic to humans, livestock, or poultry. Of interest are bacteria that are known to contaminate animal feeds, liquid animal feeds, or animal feedlots generally. Of particular interest are bacteria that also infect livestock, including swine, and poultry destined for human consumption for example but not limited to *Salmonella, Campylobacter* and *E. coli* O157:H7.

The bacteriophages, or phage components, may be provided in an aqueous solution. The aqueous solution may be any solution suitable for the purpose of the present invention. For example, the bacteriophages, or phage components, may be provided in water or in an appropriate medium as known in the art, for example LB broth, SM, TM, PBS, TBS or other common buffers as known within the art (see Maniatis et al., 1982, Molecular cloning: a laboratory manual, Cold Spring Harbor Laboratory, Cold Spring Harbor, N.Y.; which is incorporated herein by reference). For example, but without wishing to be limiting, the bacteriophages may be stored in LB broth.

By the term "matrix", it is meant any suitable solid matrix that is either soluble in water, ingestible by a mammal, or suitable for use with lotions, lubricants, gels or creams or gels. Additionally, the matrix may be non-water-soluble, provided that any absorbed phages may be released from the matrix. The matrix may be capable of adsorbing the bacteriophages, or phage components, onto its surface and releasing the bacteriophages, or phage components, in an appropriate environment. The bacteriophages, or phage components, should not adhere so strongly to the matrix that they cannot be released upon appropriate re-suspension in a medium. If the bacteriophage do associate in a non-releasable manner with the matrix, it is preferred that the matrix be present in a particulate form, from about 0.1 nm to about 100 μm in size, so as to minimize any steric hindrance between the bacteriophage and their action on the target host.

Preferably, the adsorbed, immobilized bacteriophage, phage components, or a combination thereof, are non-covalently associated with the matrix so that they may be released from the matrix when desired. Non-limiting examples of a matrix that may be used according to the present invention include skim milk powder, soya protein powder, whey protein powder, albumin powder, casein, gelatin, algal protein and other single cell proteins, plant peptone, trehalose, mannitol or other powdered sugar or sugar alcohol, charcoal, or latex beads or other inert surfaces, water-soluble carbohydrate-based materials, talc, chitin, fish cartilage, and the like, or a combination thereof. Preferably, the matrix is generally regarded as safe (GRAS). In the present description, bacteriophage, phage components, or a combination thereof, that are associated with, or adsorbed to, the matrix will be referred to as "immobilized phage" or "immobilized bacteriophage".

The bacteriophage, phage components, or a combination thereof, in aqueous solution may be applied to the matrix by any method known in the art, for example dripping or spraying, provided that the amount of the matrix exceeds the amount of aqueous bacteriophage, or phage components, solution. It is preferred that the matrix remain in a dry or semi-dry state, and that a liquid suspension of bacteriophages (or phage components) and matrix is not formed. Of these methods, spraying the bacteriophage solution over the matrix is preferred.

The antibacterial composition comprising bacteriophages, or phage components, and matrix may be dried at a temperature from about 0° C. to about 50° C. or any amount therebetween, for example at a temperature of 0, 2, 4, 6, 8, 10, 12, 14, 16, 18, 20, 22, 24, 26, 28, 30, 32, 34, 36, 38, 40, 42, 44, 46, 48, or 50° C. The antibacterial composition may be dried at a temperature from about 10° C. to about 30° C., or any amount therebetween, or from about 15° C. to about 25° C. or any amount therebetween. The drying process may also be accelerated by providing a flow of air over or through the antibacterial composition. Alternatively, the drying may be performed by heating the immobilized material under vacuum.

After a period of drying, additional aqueous solution may be applied to the matrix if desired, and the matrix re-dried. This process may be repeated as required to obtain the desired amount of phage on the matrix. The titer of phage on the matrix can be readily determined using standard techniques.

In addition, the bacteriophages or phage components adsorbed to a matrix may be embedded in a solid support. Additionally, an aqueous solution of bacteriophage may be embedded within a solid support and dried. Any suitable solid support known in the art to provide a delayed release may be used. For example, but not to be limiting in any manner, microbeads, cellulose-based material, carbohydrate-based material, shellac, polymers, methacrylates, sugars for example but not limited to mannitol and sorbitol, soya protein, whey protein, algal protein and other single cell protein, casein, gelatin, milk powder, hydroxypropylmethylcellulose phthalate (HPMCP), cellulose acetate phthalate (CAP), and hydroxypropylmethylcellulose Acetate Succinate (HPMCAS) may be used as a solid support.

The antibacterial compositions described above, whether it be immobilized bacteriophages, phage components, or a combination thereof, or immobilized bacteriophages, phage components, or a combination thereof, embedded in a solid support, may also be referred to herein as "stabilized bacteriophage or phage components" or "stablilized phage or phage components". The stabilized phage described herein may, when introduced to the proper liquid environment, preferably release the bacteriophages, phages components, or a combination thereof, such that the bacteriophages or phages components would be free in solution.

The stablilized bacteriophages, or phages components, described above may be formulated using any suitable method known in the art. For example, but not wishing to be limiting in any manner, the stabilized bacteriophages may be encapsulated, incorporated into a capsule, tabletized, or a combination thereof.

By "encapsulated", it is meant that the antibacterial composition is coated with a substance that increases the phages' resistance to the physico-chemical stresses of its environment. The stabilized phages, or phage components, may be coated with any substance known in the art, by any suitable method known in the art, for example, but not limited to the method described in US publication 2003/0109025 (Durand et al., which is incorporated herein by reference). In this method, micro-drops of the coating substance are injected into a chamber containing the component to be encapsulated, and rapidly cooled. Alternatively, a coating composition may be admixed with the one, or more than one stabilized bacteriophage, or phage components, of the present invention, with constant stirring or agitation, and cooled or dried as required.

In another alternative method of encapsulating the stabilized bacteriophages, spinning disk atomization may be used (e.g. U.S. Pat. No. 5,643,594; U.S. Pat. No. 6,001,387; U.S. Pat. No. 5,578,314; Senuma Y et. al. 2000, Biomaterials 21:1135-1144; Senuma Y., at. al. 2000, Biotechnol Bioeng 67:616-622; which are incorporated herein by reference). As would be understood by a person of skill in the art, the stabilized phages may be dispersed in either a hot melt or an organic solution containing the desired coating substance. The dispersion may then be fed onto the center of a rotating disk and the material is atomized as it leaves the periphery of the disk, resulting in encapsulated stabilized bacteriophages. The encapsulated material may then be collected using a cyclone separator, or a bed of modified food starch. The encapsulated composition may be reintroduced into the spinning disk atomizer in order to increase the thickness of the coating. In this manner, encapsulated bacteriophage compositions having different coating thickness may be obtained that exhibit varied time-released properties within a suitable environment.

Air-suspension coating is yet another example of an encapsulation method that may be used. In this method, a fluid-bed spray coater is used to apply a uniform coating onto solid particles (e.g. Jones, D. 1994, Drug Development and Industrial Pharmacy 20:3175-3206; Hall et al. 1980, The Wurster Process, in "Controlled Release Technologies: Methods, Theory, and Applications", Kyonieus A. F. ed. Vol 2, pp. 133-154, CRC Press, Boca Raton Fla.; Deasy, P. B., 1988, Crit. Rev. Ther. Drug Carrier Syst. S(2):99-139; which are incorporated herein by reference). The antibacterial composition may be suspended by an air stream that is designed to induce a smooth, cyclic-flow past a nozzle used to atomize the coating substance. Once sprayed, the antibacterial composition particles may be lifted by the air stream as the coating dries. The particles may then be circulated past the nozzle until a uniform coating is applied. The particles may be circulated until the desired film thickness has been applied. The particles may then be circulated past the nozzle until a uniform coating is obtained, or until the desired film thickness has been applied. In this manner, encapsulated bacteriophage compositions having different coating thickness may be obtained that exhibit varied timed-release properties within a suitable environment.

Alternatively, an organic solvent comprising the coating compound or substance may be used. Non-limiting examples of organic solvents include methylene chloride, methyl acetate, ethyl acetate, methyl ether ketone, acetone, alcohols and other solvents or combinations thereof.

The coating substance may be any suitable coating substance known in the art. For example, but without wishing to be limiting, the coating substance may comprise a substance with a melting temperature between about 20° C. and about 100° C., or any temperature therebetween, for example between about 30° C. and about 80° C., or any temperature therebetween, or between about 60° C. and about 80° C., or any temperature therebetween; for example, the melting temperature may be 20, 22, 24, 26, 28, 30, 32, 34, 36, 38, 40, 42, 44, 46, 48, 50, 52, 54, 56, 58, 60, 62, 64, 66, 68, 70 72, 74, 76, 78, 80, 82, 84, 86, 88, 90, 92, 94, 96, 98, or 100° C., or any amount therebetween. If the coating substance is to be ingested or used for an oral application, then it is preferred that the substance is a food grade substance. However, the stabilized bacteriophages, or phage component, of the present invention may also be coated with other substances that are not food grade, depending on the antibacterial composition's intended use. For example, the antibacterial composition may be encapsulated in an emulsion-compatible coating for use in lotions or lubricants or creams or gels. Other additive molecules may be added to the coating substance; such additive may include antioxidants, sugars, proteins or other synthetic material.

Non-limiting examples of suitable coating substances include lipid-based materials such as vegetable fatty acids; fatty acids such as palmitic acid and stearic acid, for example Stéarine™; animal waxes, for example beeswax; vegetable waxes, for example Carnauba wax or Candelilla wax; and wax derivatives, other lipids or lipid derivatives, and shellac.

Additional coating substances may also be used, for example, non lipid-based materials (see for example, U.S. Pat. Nos. 6,723,358; and 4,230,687, both of which are incorporated herein by reference), for example sugars, cellulose-based components, or other carbohydrate-based components that may be water soluble. For example, and without wishing to be limiting in any manner, Hydroxypropylmethylcellulose phthalate (HPMCP), Cellulose acetate phthalate (CAP), and Hydroxypropylmethylcellulose Acetate Succinate (HPMCAS) may be used as non-lipid based materials suitable for encapsulation.

Polymers may also be used to encapsulate the stabilized bacteriophages or phage components. Any polymer known in the art may be used, and may be chosen for immediate release of the bacteriophages, or phage components, or for controlled release. For example, and without wishing to be limiting in any manner, appropriate polymers may include those disclosed by Mehta (U.S. Pat. No. 6,926,909), Hussain et al (U.S. Pat. No. 6,649,187), or Yang et al (U.S. Pat. No. 5,576,022), all of which are incorporated herein by reference. In a non-limiting example, polymers such as poly(vinyl acetate) phthalate (PVAP), methacrylate-based, or shellac may be used.

As would be understood by a person of skill in the art, one or more than one of the coating substances may be used. For example, the stabilized bacteriophages, or phage components, may be encapsulated using or embedded in one type of coating substance, followed by a second encapsulation, or over-coating, using another coating substance. In a non-limiting example, the stabilized bacteriophages, or phage components may first be encapsulated with or embedded in a cellulose-based component, followed by over-coating with a lipid-based material; alternatively, the stabilized bacteriophages, or phage components may first be encapsulated with or embedded in a polymer, followed by an over-coating with a lipid-based material.

The process of lipid-based encapsulation protects the bacteriophages, phage components, or both, to some extent from a harsh environment the bacteriophages or components may be exposed to, for example, the low pH environment over a range of fermenting liquid feed conditions, or the digestive system of an animal. The lipid-based material selected for encapsulation should also exhibit the property that it breaks down within a desired environment so that the bacteriophages or phage components are released, providing one form of timed-release. For example, digestive enzymes may degrade the encapsulating material and assist in the release of the bacteriophages or phage components within the gut of an animal, or enzymes within the fermenting liquid feed, for example, may assist in the release of some of the bacteriophages or phage components from encapsulation. Other mechanisms of release include pH-based, or reaction with chemicals released within a defined chamber such as bile acids. As a result, several materials for encapsulating the bacteriophages or phage components may be used so that if desired, there is selected release of the bacteriophage, while at the same time protecting the bacteriophages, or phage components. Varying the thickness of the coating of encapsulated bacteriophages or phage components may also provide additional timed-release characteristics.

In addition, a non-lipid-based or polymer encapsulation material may dissolve in water, thereby releasing bacteriophages or phage components immediately, or soon after mixing with the liquid feed medium. The bacteriophages or phage components may also be released in a time-controlled fashion depending upon the material and formulation selected, or whether the preparations are provided within a capsule or tablet form. The capsule or tablet formulations may assist in the timed-release of the stabilized bacteriophages or phage components within the animal or other environment. Therefore, mixtures of controlled release bacteriophages, phage components, or both that are admixed, encapsulated, or both, with different materials may be combined and mixed with animal feed, liquid animal feed, or otherwise administered to an animal.

The stabilized bacteriophage, phage components, or a combination thereof, the encapsulated bacteriophage, phage components, or a combination thereof, or a mixture of both the stabilized and encapsulated phage, may also be provided in a capsule form. By "capsule form", it is meant that the stabilized bacteriophage, encapsulated phages, stabilized or encapsulated phage components, or a combination thereof, are provided in a capsule for example a soft capsule, which may be solubilized within an aqueous environment. The capsule may be made of any suitable substance known in the art, for example, but not limited to gelatin, shellac, methacrylate derivatives, a synthetic, or other compounds, and may comprise additional components such as stabilizers and colorants, as would be known to a person of skill in the art.

The stabilized bacteriophage, phage components, or a combination thereof, the encapsulated bacteriophages, phage components, or a combination thereof, may also be provided in a tablet form. By "tablet form", it is meant that the stabilized phages, or phage components, or a mixture of both the stabilized and encapsulated phage are provided in a pressed tablet that dissolves in an aqueous environment. The tablet may be made of any suitable substance known in the art, by any suitable method known in the art. For example, the tablet may comprise binders and other components necessary in the production of a tablet as are known to one of skill in the art. The tablet may be an immediate release tablet, where the bacteriophages or phage components are released into the liquid feed upon dissolution of the tablet, or may comprise a timed-release composition, where the bacteriophages or phage components are released within an aqueous environment in a time-dependent manner. See WO 02/45695; WO 03/051333; U.S. Pat. No. 4,601,894; U.S. Pat. No. 4,687,757, U.S. Pat. No. 4,680,323, U.S. Pat. No. 4,994,276, U.S. Pat. No. 3,538,214, U.S. (which are incorporated herein by reference) for several examples of time-release formulations that may be used to assist in the time controlled release of bacteriophages, or phage components within aqueous environments.

Tablet formulations may comprise a hydrodynamic fluid-imbibing polymer for example but not limited to acrylic-acid polymers with cross-linking derived from allylsucrose or allylpentaeritbritol, including water-insoluble acrylic polymer resins. Single compounds or a blend of compounds from this group of polymers include for example, but not limited to Carbopol.®.971-P, Carbopol.®.934-P, Carbopol.®.974P and Carbopol.®.EX-507 (GF Goodrich, or any other commercially available brand with similar properties, may be used). Preferably, the acrylic-acid polymers have a viscosity from about 3,000 centipoise to about 45,000 centipoise at 0.5% w/w concentration in water at 25EC, and a primary particle size range from about 3.00 to about 10.00 microns in diameter, as determined by Coulter Counter; highly cross-linked or lightly cross-linked starch derivatives crosslinked by Epichlorhydrin or Phosphorous oxychloride ($POCl_3$) or Sodium trimetaphosphate either singly or in blends; polyglucans such as amylose, dextran, pullulan succinates and glutarates containing diester-crosslinks either singly or in blends; diether crosslinked polyglucans such as those disclosed in U.S. Pat. Nos. 3,208,994 and 3,042,667 (which are incorporated herein by reference); crosslinked polyacrylate resins such as, but not limited to, potassium polyacrylate; and water swellable crosslinked polymer compositions of crosslinked polyethylenimine and or crosslinked polyallyamine.

Methods of preparation, for example of Carbopol.®.934-P,—a polymer of acrylic acid lightly cross-linked with polyallyl ether of sucrose having an average of 5.8 allyl groups per each sucrose molecule, may be found in U.S. Pat. Nos. 2,909, 462; 3,033,754; 3,330,729; 3,458,622; 3,459,850; and 4,248, 857 (which are incorporated herein by reference). When Carbopol.®.971-P is used, the preferred viscosity of a 0.5% w/w aqueous solution is 2,000 centipoise to 10,000 centipoise. More preferably, the viscosity of a 0.5% w/w aqueous solution is 3,000 centipoise to 8,000 centipoise. When Carbopol.®.934-P is used, the preferred viscosity of a 0.5% w/w aqueous solution is 20,000 centipoise to 60,000 centipoise, more preferably, the viscosity of a 0.5% w/w aqueous solution is 30,000 centipoise to 45,000 centipoise Cross-linked starch derivatives (crosslinked by Epichlorhydrin or Phosphorous oxychloride ($POCl_3$) or Sodium trimetaphosphate) include high amylose starch containing varying degrees of crosslinking. These compounds and their methods of preparation are known in the art, for example, U.S. Pat. No. 5,807,575 and U.S. Pat. No. 5,456,921 (which are incorporated herein by reference), and Rutenberg and Solarek (M. W. Rutenberg and D. Solarek, "Starch derivatives: production and uses" in Starch Chemistry and Technology, $2^{nd}$ Edition, Chapter X, Pages 311-379, R. L. Whistler, J. N. BeMiller and E. F. Paschall, Academic Press, 1984; which is incorporated herein by reference).

Tablet formulations comprising the hydrodynamic fluid-imbibing polymer may also be formulated with an agent that expands rapidly upon exposure to fluid, for example, a rapid expansion polymer. For example, this agent may comprise hydrophilic cross-linked polymers that are capable of rapid capillary uptake of water and a limiting volume expansion. Non-limiting examples of rapid expansion polymers include: single compounds or combinations derived from cross-linked N-vinyl-2-pyrollidone (PVP) selected from a group of chemically identical polyvinylpolypyrrolidone such as Polyplasdone.®.XL, Polyplasdone.®.XL-10, Polyplasdone.®.INF-10 (International Specialty Products). Prefreably, the cross-linked N-vinyl-2-pyrollidone has a particle size from about 9 microns to about 150 microns; and cross-linked cellulose derivatives selected from a group of hydrophilic compounds such as cross-linked carboxymethyl cellulose (for example croscarmellose), sodium starch glycolate or a combination thereof.

The capsule or tablet formulations may comprise one or more stabilized bacteriophage, phage components, or a combination thereof, encapsulated bacteriophage, phage components, or a combination thereof, or a mixture of stabilized and encapsulated bacteriophage, phage components, or a combination thereof. For example, the capsule or tablet may comprise: bacteriophage, phage components, or a combination thereof, adsorbed to a matrix; bacteriophages, phage components, or a combination thereof, adsorbed to a matrix and encapsulated; bacteriophage, phage components, or a combination thereof, adsorbed to a matrix and embedded in a solid support; bacteriophages, phage components, or a combination thereof, adsorbed to a matrix, embedded in a solid support, and encapsulated; or mixtures of any of the above.

By "controlled release" or "timed release", it is meant that the agent administered to the animal is released from the formulation in a time-dependent manner. For example, the one or more than one bacteriophage or phage component may be stabilized bacteriophage, encapsulated bacteriophage, stabilized phage components, encapsulated phage components, bacteriophage or phage components that are provided in capsule form, bacteriophages or phage components that are provided in tablet form, bacteriophages or phage components that are encapsulated, in capsules, in tablets, or a combination thereof, wherein the encapsulated, capsule, or tablet forms of the bacteriophages or phage components comprise compositions that release the bacteriophages or phage components at different rates within the appropriate environment, for example an aqueous environment. The compositions of the encapsulation material, capsule, or tablets may include polymers, waxes, gels, compounds that imbibe water, repel water, or both, fatty acids, sugars, proteins or synthetic materials, to effect release of an agent within the composition in a controlled manner. Various controlled release compositions comprising bacteriophages or phage components may be used so that the bacteriophages or phage components may be released prior to administration to an animal, during passage through the digestive tract of the animal, or after leaving the animal.

The antibacterial compositions of the present invention exhibit desirable storage properties and may be used in a variety of applications. For example, which is not to be considered limiting in any manner, the antibacterial compositions may be used for human, veterinary, aquacultural, and agricultural applications. For example, stabilized bacteriophage, or stabilized bacteriophage embedded in a solid support may be admixed with fish feed for use within aquaculture applications, including farming and maintenance of fish for food and fish for decorative purposes, such as tropical fish. Furthermore, the compositions may be used for the treatment of trees and plants, and environmental applications. For example, the antibacterial composition may be mixed with the feed of livestock, birds, poultry, domestic animals and fish, to aid in reducing the shedding of target bacteria. The phage compositions of the present invention may be mixed with other additives or supplements applied to animal feed as part of the daily feed regime, as needed. Thus, settling of the bacteriophages, or phage components, in the feed could be avoided. Alternatively, the adhesion of the feed or the bacteriophage, or both, may be enhanced to provide improved mixing and delivery. In another example, the antibacterial material, alone or in combination with a pharmaceutically acceptable carrier or excipient that will not affect the activity or specificity of the bacteriophages, or phage components, could be used as an oral, topical or nasal medication for humans, mammals, or avian species. The encapsulated bacteriophage may also be used within phage therapy applications including human, veterinary, agricultural applications. Furthermore, encapsulated bacteriophage may be admixed with fish feed for use within aquaculture applications, including farming and maintenance of fish for food and fish for decorative purposes, such as tropical fish.

Therefore, the present invention provides an antibacterial composition comprising one or more than one strain of bacteriophage, or one or more than one phage component, adsorbed onto a matrix, and optionally, for example form 0% to about 95% (by weight) or any amount therebetween, a pharmaceutically acceptable carrier, a cream, lotion, gel, or a combination thereof. The present invention also provides an antibacterial composition comprising one or more than one strain of bacteriophage, one or more than one phage component, or a combination thereof, adsorbed onto a matrix, encapsulated or present within a time-release formulation. The encapsulated, or timed-release bacteriophage formulation may be dispersed within a pharmaceutically acceptable carrier, a cream, lotion, gel, or a combination thereof.

The present invention also provides a kit comprising a sterile vial comprising an antibacterial composition comprising one or more than one strain of bacteriophage, one or more than one phage component, or a combination thereof, adsorbed onto a matrix, and a vial of sterile water or media for dissolving the composition. The present invention further provides a kit comprising an antibacterial composition, the antibacterial composition comprising one or more than one strain of bacteriophage, one or more than one phage component, or a combination thereof, adsorbed onto a matrix and encapsulated or within a time-release formulation, and a vial of sterile water or media for dissolving the composition.

The present invention also provides a method of treating a wound or a skin infection comprising, applying an antibacterial composition or an encapsulated antibacterial composition as described herein, comprising one or more than one strain of bacteriophage, one or more than one phage component, or a combination thereof, adsorbed onto a matrix, a pharmaceutically acceptable carrier, a cream, lotion, gel, or a combination thereof, to the wound, or skin infection. The present invention also provides a method of treating a wound or a skin infection comprising, applying an antibacterial composition as described herein, for example an encapsulated antibacterial composition, or a time-release antibacterial composition, comprising one or more than one strain of bacteriophage, one or more than one phage component, or a combination thereof, a pharmaceutically acceptable carrier, a cream, lotion, gel, or a combination thereof, to the wound, or skin infection. Furthermore, the antibacterial composition of the present invention may be used to treat a bacterial infection within an animal, including human. Such treatment may involve introducing the antibacterial composition to the animal nasally or orally, for example the composition may be administered as a powder inhalant, or as an additive in feed.

The present invention also provides a composition comprising an animal feed admixed with an immobilized antibacterial composition, an antibacterial composition that has been encapsulated, or a time-released, or control-released formulation of an antibacterial composition, where the composition comprises one or more than one strain of bacteriophage. The animal feed may be selected from the group consisting of a bird feed, a fish feed, a porcine feed, a livestock feed, a poultry feed, a domestic animal feed, and a food for aquaculture.

The present invention will be further illustrated in the following examples.

EXAMPLES

Example 1

Isolation, Amplification and Titration of Phase

Bacteriophages were isolated from manure samples obtained from dairy and beef farms across Canada. Manure samples were allowed to react with *E. coli* O157:H7 and plated onto agar plates. Any phage plaques obtained were isolated and purified as per standard phage purification protocols (Maniatis et al (1981) Molecular cloning: a laboratory manual, Cold Spring Harbor Laboratory, Cold Spring Harbor, N.Y.).

Purified phages isolated as outlined in Example 1 were amplified using the isolation strain of *E. coli* O157:H7. Purified phage and bacteria were mixed together, let stand at room temperature for 10 minutes, and amplified according to standard protocols commonly used in the art (Maniatis et al (1981) Molecular cloning: a laboratory manual, Cold Spring Harbor Laboratory, Cold Spring Harbor, N.Y.). Amplified samples in LB broth were filter sterilized and used.

Concentrations of bacteriophage solutions were determined using standard phage titration protocols (Maniatis et al (1981) Molecular cloning: a laboratory manual, Cold Spring Harbor Laboratory, Cold Spring Harbor, N.Y.). Preparations containing phages were diluted with LB, mixed and incubated with E. coli O157:H7 for 10 minutes and plated onto agar plates. The concentration of phages was determined from the number of plaques obtained at the different dilutions and multiplying with the appropriate dilution factor.

Example 2

Immobilization of Phages

E. coli O157:H7 specific phages P10 and R4, prepared as described in example 1, were immobilized on two different matrices: powdered milk (fat free) and soya protein, plant peptone. Milk powder (Carnation) and soya protein (Supro) were obtained off-the-shelf from local food stores. Identical protocols were used for both materials.

50 g of powder (powdered milk, soya protein, or plant peptone) was spread in a glass dish. Phages in solution were uniformly sprayed onto each powdered matrix. Varying titers of phages, ranging from $10^5$ pfu/g to $10^9$ pfu/g, were used with powdered milk, each yielding similar results. The phage-powder was mixed and dried at 37° C. for 2 hours, or until completely dried. The resulting bacteriophage composition was ground into a fine powder, with particle sizes in the range of 50-600 μm and an average particle size of 200 μm. 0.5 grams of each powdered bacteriophage composition was re-suspended in 10 ml of reverse-osmosis (RO) water and the recovery of phages tested. Powdered milk, powdered soya protein, or plant peptone, in the absence of bacteriophages was used as a control. Slight clumping of the bacteriophage composition comprising soy protein was observed when re-suspended in the RO water. The results for bacteriophage compositions prepared using dry milk power as the matrix are presented in FIG. 1. Results for bacteriophage compositions prepared using soy protein as the matrix are presented in FIG. 2, and plant peptone are shown in FIG. 4.

For phage immobilized on powdered milk, the results show that phage can be recovered from the bacteriophage composition and no loss in activity was observed. FIG. 1 shows that the phage titer obtained after immobilization ("After") is similar to the amount of phage added to the powder ("Before"). Similar results were observed for bacteriophage compositions comprising soy protein (FIG. 2; After—immobilized phage; Before—amount of phage added to matrix). For phage immobilized on soya protein, a slight decrease in phage recovery was observed which may be due to caking of the soya protein upon addition to RO water. Again, as shown in FIG. 4 the phage titer obtained after immobilization ("After") is similar to the amount of phage added to the powder ("Before") using plant peptone as a matrix.

These results also show that immobilized phages are readily released from a matrix when introduced to an aqueous medium.

Example 3

Encapsulation of Bacteriophage Compositions

Bacteriophage compositions are prepared as described in Example 2, and are provided as microcapsules or microspheres. Generally, microcapsules are produced by embedding the bacteriophage composition in a solid support including, soya protein, or milk powder (other solid supports include microbeads, cellulose-based material, carbohydrate-based material, mannitol, sorbitol, whey protein, algal protein, single cell protein, casein, gelatin, shellac) with a particle size of approximately 1 mm. Microspheres are produced by grinding the stabilized phage preparation and mixing it in lipid melt to produce microspheres of from about 0.01 mm to about 1 mm.

The microcapsules are then encapsulated by any suitable method, for example, spinning-disk atomization, air-suspension coating using a fluid-bed spray coater, bacteriophage may also be coated using the method disclosed in US 2003/0109025 (which is incorporated herein by reference in its entirety), or by mixing within an organic solution comprising a solvent, for example but not limited to methylene chloride, methyl acetate, ethyl acetate, methyl ether ketone, acetone, alcohols and other solvents or combinations thereof, containing the coating substance.

Briefly, for spinning-disk atomization, phage compositions are dispersed in either a hot melt or an organic solution containing the coating substance. The dispersion is fed onto the center of a rotating disk and the material is atomized as it leaves the periphery of the disk. The encapsulated material is collected using a cyclone separator or a bed of modified food starch. In air-suspension coating, a fluid-bed spray coater is used. Solid particles are suspended by an air stream that induces a smooth, cyclic-flow past a nozzle that atomizes the coating substance. Once sprayed, the particles are lifted by the air stream as the coating dries. The particles are circulated past the nozzle until a uniform coating is applied. The particles are circulated until the desired film thickness has been applied. Microspheres are encapsulated using spinning-disk atomization.

Each of the microcapsules and microspheres are encapsulated with each of the following coating substances: palmitic acid, stearic acid, shellac over-coated with palmitic acid, stearic acid, HPMCP over-coated with palmitic acid, stearic acid, CAP over-coated with palmitic acid, stearic acid, HPMCAS over-coated with palmitic acid, stearic acid, PVAP over-coated with palmitic acid, stearic acid, and methacrylate over-coated with palmitic acid, stearic acid. Other fatty acids may also be used for over-coating.

Once the coating operation is complete, the encapsulated stabilized phage particles are collected and stored in airtight containers.

The effect of encapsulation on the titer of bacteriophage compositions is evaluated by determining the activity of the stabilized phage preparation before ("Before") and after ("After") encapsulation. For this analysis, encapsulated bacteriophages are re-suspended, and ground using a blender. The re-suspended encapsulated stabilized bacteriophages are blended, or treated with the appropriate release mechanism, for example alternation in pH, or exposure to an aqueous environment, in order to disrupt the encapsulated particles and release the bacteriophages. For bacteriophage release by blending, 0.5 g of encapsulated stabilized phages is mixed with 45.5 ml of re-suspension media (LB Broth or RO Water), and 250 μl of antifoam agent is added to prevent foaming upon grinding.

The results demonstrate that bacteriophages can be recovered from an encapsulated bacteriophage composition, and encapsulation does not inactivate the immobilized phage.

Example 4

Stability and Release of Encapsulated Bacteriophages

Phages are encapsulated as described in Example 3. The release of encapsulated stabilized phages upon physical or chemical disruption is tested in the following manner: 0.5 g of encapsulated stabilized phage is mixed with 45.5 ml of resuspension media (LB Broth or RO Water). 250 μl of antifoam agent is used to prevent foaming upon grinding. A control sample of encapsulated stabilized phages is prepared as described above, but not subjected to grinding, to determine the non-specific leaching of encapsulated bacteriophages within the re-suspension medium.

The stability of the encapsulated bacteriophages at low pH is also examined. After re-suspension (as outlined above), the encapsulated stabilized phages are incubated for 30 or 60 min at pH 2.15, neutralized to pH 7.0 using NaOH, then ground using a blender; another sample (control) is resuspended and immediately ground. Both the control and test samples are filter sterilized using a 0.45 μm syringe filter prior to use.

The results demonstrate that bacteriophages may be released following disruption of encapsulated bacteriophage particles. Furthermore, these results shows that encapsulated bacteriophage may be exposed to a pH of 2.15 for prolonged period of time, with little or no loss in activity (titer). The results for non-encapsulated and non-stabilized bacteriophages are consistent with the results of Jepson and March (2004, Vaccine, 22:2413-2419), where a dramatic loss of viability of bacteriophages was observed after only 5 minutes at pH below pH 2.2. This loss in activity is obviated by encapsulation of the bacteriophages as described in the present invention.

Example 5

Stability of Immobilized Phage

Bacteriophages were immobilized on a matrix, in this case milk powder as described in Example 2 and the material was stored at either room temperature (RT) or at 4° C. (4C) in airtight containers. Samples were obtained at different time points, and phage titers determined, over a period of 10 months. The initial phage concentration was $3 \times 10^6$ pfu/g.

Figure 3:
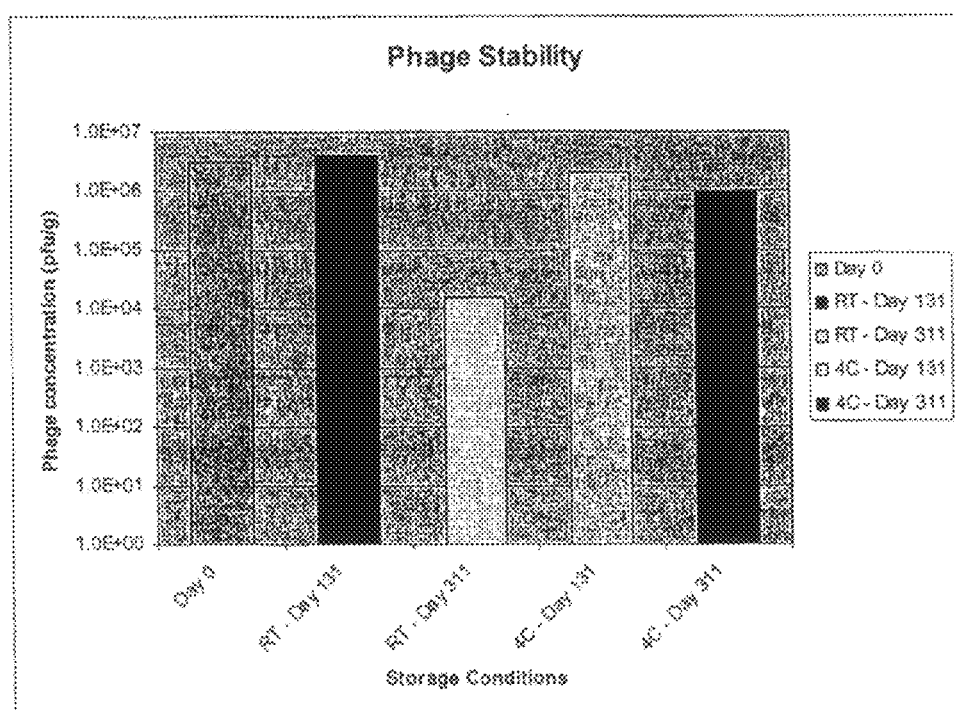
FIG. 3 shows stability of immobilized phages over a period of 4.5 months (131 days) and 10 months (311 days) when stored at room temperature (RT) or at 4° C.
Figure 4:
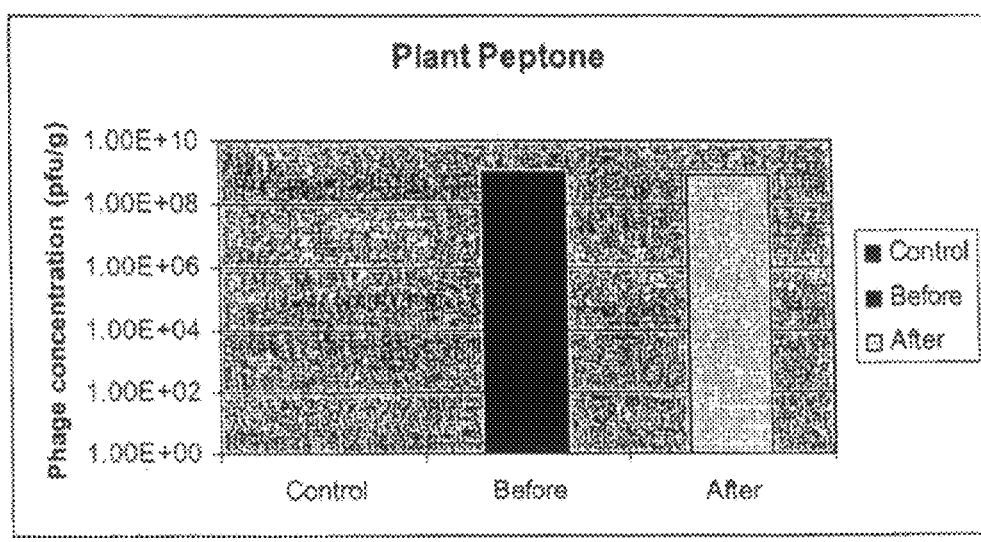
FIG. 4 shows the titer of phage applied to the plant peptone protein powder (Before) and that obtained after immobilization and resuspension (After).

FIG. 3 shows that the immobilized phages (bacteriophage composition) are stable at either room temperature or 4° C. for at least 131 days (4.5 months), and is stable for at least 311 days (10 months) at 4° C. Addition of a desiccant, or storage of the bacteriophages in a desiccated environment may further increase the viability of the bacteriophage composition.

Example 6

Immobilized Phage in Cream and Lotion

The viability of immobilized phages (bacteriophage composition) incorporated into a lotion or cream was also investigated.

Two grams of lotion (Vaseline hand lotion) or cream (GlycoMed cream) was weighed into a sterile Petri dish. The desired pfu/g of immobilized phage, P10 and R26, was added to the lotion or cream and mixed thoroughly. Bacteria were spread on LB-agar plates and allowed to grow at 37° C. for two to three hours to form a uniform lawn. Two cm² pieces of filter paper, two per plate, were placed onto the lawn and the lotion comprising bacteriophages, or the cream comprising bacteriophages, were each spread over one filter paper. Aliquots of the lotion or cream without phage (control) were spread onto the other filter paper to determine whether the lotion or cream had antimicrobial properties. A spot of lotion or cream containing bacteriophages was also placed directly on the bacterial lawn. Several dilutions of the bacteriophages within each of the lotion or cream were tested. The plates were incubated overnight at 37° C. Each treatment was scored as a "Yes" or a "No", depending on the presence or absence of the zone of inhibition, respectively, and the results are presented in Table 1.

TABLE 1

Efficacy of bacteriophage compositions (immobilized phages) in hand lotion or cream.

| Material | Technique | Phage | pfu/g | | | |
|---|---|---|---|---|---|---|
| | | | 1.00E+07 | 1.00E+06 | 1.00E+05 | 1.00E+04 |
| Lotion | Filter | P10 | Yes | Yes | Yes | Yes (5/6) |
| Lotion | Spot | P10 | Yes | Yes | Yes | Yes (1/3) |
| Lotion | Filter | — | No | No | No | No |
| Cream | Filter | P10 | Yes | Yes | Yes | Yes |
| Cream | Spot | P10 | Yes | Yes | Yes | Yes |
| Cream | Filter | — | No | No | No | No |
| Lotion | Filter | R26 | Yes | Yes | Yes (2/3) | Yes (1/3) |
| Lotion | Spot | R26 | Yes | Yes | Yes | No |
| Lotion | Filter | — | No | No | No | No |
| Cream | Filter | R26 | Yes | Yes | Yes | Yes |
| Cream | Spot | R26 | Yes | Yes | Yes | Yes |
| Cream | Filter | — | No | No | No | No |

A zone of inhibition of bacterial growth was observed where activity of phages could be recovered. Lotion and cream containing encapsulated immobilized phages both show antibacterial activity, while the lotion or cream alone shows no inhibition of bacterial growth. These results indicate that bacteriophage compositions prepared according to the present invention may be admixed within lotion and cream preparations for use as antibacterial lotions, lubricants, gels or creams.

Improved stability of the bacteriophages is observed for immobilized bacteriophages in creams.

Example 7

Delivery of Active Bacteriophages

*E. coli* 0157 specific bacteriophages are encapsulated as previously described in Example 3. The encapsulated phages are then mixed with other supplements and added to animal feed in an amount of about 1-50 g per animal per dose. The feed is then fed to the animal once per day for 5 days prior to slaughter. Alternatively, a maintenance dose is given to the animal every 1-3 days.

Analysis of the animal's manure reveals a decrease in the *E. coli* 0157 in the animal, indicating that active bacteriophages are delivered to the gut of the animal.

All citations are hereby incorporated by reference.

The present invention has been described with regard to one or more embodiments. However, it will be apparent to persons skilled in the art that a number of variations and modifications can be made without departing from the scope of the invention as defined in the claims.

The embodiments of the invention in which an exclusive property of privilege is claimed are defined as follows:

1. An antibacterial composition consisting essentially of one or more than one bacteriophage adsorbed onto a dry matrix of milk powder, wherein when the composition is stored at room temperature for up to 131 days, all bacteriophage remain viable.

2. A composition comprising the antibacterial composition of claim 1 and a pharmaceutically acceptable carrier.

3. A kit comprising a sterile vial comprising the composition of claim 2 and a vial of sterile water for dissolving the composition.

4. A composition comprising an animal feed admixed with the antibacterial composition of claim 1.

5. The composition of claim 4, wherein the animal feed is selected from the group consisting of a human food, bird feed, a fish feed, a porcine feed, a livestock feed, a poultry feed, a domestic animal feed, and a food for aquaculture.

6. The antibacterial composition of claim 1, wherein the composition is formulated within a tablet.

7. The antibacterial composition of claim 6, wherein the tablet further comprises components that permit controlled release of the one or more than one bacteriophage.

8. The antibacterial composition of claim 1, wherein the antibacterial composition is embedded in a solid support.

9. The antibacterial composition of claim 8, wherein the solid support is selected from the group consisting of a microbead, cellulose-based material, carbohydrate-based material, shellac, methacrylates, sugar, mannitol, sorbitol, soya protein, whey protein, algal protein, single cell protein, casein, gelatin, and milk powder.

10. The antibacterial composition according to claim 1, wherein the antibacterial composition is coated with a substance that increases the resistance of the one or more than one bacteriophage to the physico-chemical stresses of the environment of a fermenting animal feed or the digestive system of an animal.

11. The antibacterial composition according to claim 10, wherein the substance is a polymer for controlled release of the one or more than one bacteriophage.

12. The antibacterial composition according to claim 11, wherein the polymer is a methacrylate-based polymer.

\* \* \* \* \*